US00PP31567P2

(12) United States Plant Patent
Hartman

(10) Patent No.: US PP31,567 P2
(45) Date of Patent: Mar. 17, 2020

(54) ***CALADIUM* PLANT NAMED 'HEART AND SOUL'**

(50) Latin Name: ***Caladium* X *hortulanum***
Varietal Denomination: Heart and Soul

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/350,106

(22) Filed: Sep. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/00
See application file for complete search history.

(56) References Cited

PUBLICATIONS

Anthony. Cool *Caladiums* brighten landscapes, The Eagle 2018, retrieved on Jul. 11, 2019, retrieved from the Internet at https://www.theeagle.com/brazos_life/our_neighbors/cool-caladiums-brighten-landscapes/article_730bb77a-d189-57ca-bda2-e1bbfbd120ad.html, 4 pp. (Year: 2018).*

Classic *Caladiums* New *Caladiums* from Classic Recent Introductions from our Classic Labs, retrieved on Jul. 11, 2019, retrieved from the Internet at https://www.classiccaladiums.com/new_caladium_varieties.htm, 2 pp. (Year: 2019).*

Imgrum 2018, Classic *Caladiums* photos & videos, retrieved on Jul. 11, 2019, retrieved from the Internet at https://www.imgrumweb.com/hashtag/classiccaladiums, 2 pp. (Year: 2018).*

* cited by examiner

*Primary Examiner* — June Hwu
(74) *Attorney, Agent, or Firm* — C. A. Whealy

(57) ABSTRACT

A new and distinct cultivar of *Caladium* plant named 'Heart and Soul', characterized by its short to intermediate height; upright and mounding plant habit; dense and bushy appearance; vigorous growth habit and rapid growth rate; lance-type leaves that are dark green in color with greyed purple-colored venation, white, green, red and greyed purple-colored interveinal areas, and dark red-colored random spots; undulate margins give a ruffled appearance to the leaves; and petioles that are light greyed red to light greyed orange in color with greenish brown-colored stipples and streaks.

4 Drawing Sheets

Botanical designation: *Caladium* X *hortulanum*.
Cultivar denomination: 'HEART AND SOUL'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'Heart and Soul'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'White Wonder', disclosed in U.S. Plant Pat. No. 21,044, as the female, or seed, parent with *Caladium* X *hortulanum* 'Gingerland', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Heart and Soul'. These characteristics in combination distinguish 'Heart and Soul' as a new and distinct *Caladium* plant:

1. Short to intermediate in height and upright and mounding plant habit; dense and bushy appearance.
2. Vigorous growth habit and rapid growth rate.

3. Lance-type leaves that are dark green in color with greyed purple-colored venation, white, green, red and greyed purple-colored interveinal areas, and dark red-colored random spots; undulate margins give a ruffled appearance to the leaves.
4. Petioles that are light greyed red to light greyed orange in color with greenish brown-colored stipples and streaks.

Plants of the new *Caladium* differ primarily from plants of the female parent, 'White Wonder', in the following characteristics:

1. Leaves of plants of the new *Caladium* have undulate margins and are folded upright along the midvein whereas leaves of plants of 'White Wonder' are flatter with broader undulations.
2. Plants of the new *Caladium* and 'White Wonder' differ in leaf color as leaves of the new *Caladium* are dark green in color with greyed purple-colored venation, white, green, red and greyed purple-colored interveinal areas, and dark red-colored random spots whereas leaves of 'White Wonder' are white to grey-green in color with light pink to white-colored venation and dark green-colored borders.
3. Plants of the new *Caladium* and 'White Wonder' differ in leaf petiole color as petioles of the new *Caladium* are light greyed red to light greyed orange in color with greenish brown-colored stipples and streaks whereas petioles of 'White Wonder' are tan green in color with darker colored stripes.

Plants of the new *Caladium* differ primarily from plants of the male parent, 'Gingerland', in the following characteristics:

1. Plants of the new *Caladium* are shorter, denser and bushier than plants of 'Gingerland'.
2. Plants of the new *Caladium* grow more rapidly than plants of 'Gingerland'.
3. Plants of the new *Caladium* and 'Gingerland' differ in leaf color as leaves of the new *Caladium* are dark green in color with greyed purple-colored venation, white, green, red and greyed purple-colored interveinal areas, and dark red-colored random spots whereas leaves of 'Gingerland' have white-colored interveinal areas, white and pink-colored venation, dark red-colored spots and dark green-colored borders.

Plants of the new *Caladium* can be compared to plants of *Caladium* X *hortulanum* 'Day Dreamer', disclosed in U.S. Plant Pat. No. 29,563. In side-by-side comparisons, plants of the new *Caladium* differ primarily from plants of 'Day Dreamer' in the following characteristics:

1. Plants of the new *Caladium* are short to intermediate in height whereas plants of 'Day Dreamer' are short in height.
2. Leaves of plants of the new *Caladium* have undulate margins and are folded upright along the midvein whereas leaves of plants of 'Day Dreamer' are less wavy with broader undulations.
3. Plants of the new *Caladium* and 'Day Dreamer' differ in leaf color as leaves of the new *Caladium* are dark green in color with greyed purple-colored venation, white, green, red and greyed purple-colored interveinal areas, and dark red-colored random spots whereas leaves of 'Day Dreamer' are medium green in color with greenish white-colored venation surrounded with white areas and interveinal areas that are white variably tinged with purplish pink in color with random dark red-colored flecks and spots.

Plants of the new *Caladium* can be compared to plants of *Caladium* X *hortulanum* 'Miss Muffet', not patented. In side-by-side comparisons, plants of the new *Caladium* differ primarily from plants of 'Miss Muffet' in the following characteristics:

1. Plants of the new *Caladium* are taller, denser and bushier than plants of 'Miss Muffet'.
2. Plants of the new *Caladium* and 'Miss Muffet' differ in leaf color as leaves of the new *Caladium* are dark green in color with greyed purple-colored venation, white, green, red and greyed purple-colored interveinal areas, and dark red-colored random spots whereas leaves of 'Miss Muffet' are pale green tinged with pink in color with a deep reddish pink-colored blush in the center.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Heart and Soul' in a container and grown in a shadehouse (tuber de-eyed).

The photograph at the top of the second sheet is a comparison view of typical potted plants of the female parent, 'White Wonder' (left), 'Heart and Soul' (center) and the male parent, 'Gingerland' (right).

The photograph at the bottom of the second sheet is a comparison view of typical potted plants of 'Day Dreamer' (right), 'Heart and Soul' (center) and 'Miss Muffet' (left).

The photograph at the top of the third sheet is a comparison view of typical plants of 'Heart and Soul' grown in containers; the plant on the left has not had its tuber de-eyed and the plant on the right has had its tuber de-eyed prior to planting.

The photograph at the bottom of the third sheet is a side perspective view of typical plants of 'Heart and Soul' grown in an open production field.

The photograph at the top of the fourth sheet is a close-up view of typical freshly-harvested tubers with roots and leaf petioles of 'Heart and Soul'.

The photograph at the bottom of the fourth sheet is a close-up view of a typical inflorescence of 'Heart and Soul'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26°

C. and light levels ranged from 10,000 to 12,000 foot-candles. Plants grown in the shadehouse were six to seven weeks old and plants grown in the outdoor nursery were 8.5 months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Heart and Soul'.

Parentage:

*Female, or seed, parent.*—*Caladium* X *hortulanum* 'White Wonder', disclosed in U.S. Plant Pat. No. 21,044.

*Male, or pollen, parent.*—*Caladium* X *hortulanum* 'Gingerland', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic to ovate in shape. Height: About 4.1 cm. Diameter: About 6.4 cm to 8.4 cm. Segment height: About 2.1 cm to 2.9 cm. Segment diameter: About 2.2 cm to 2.4 cm. Axillary buds size: About 3 mm by 5 mm. Texture: Thick, starchy; somewhat brittle. Color: Epidermis, freshly-harvested: Close to 158D. Epidermis, dried: Close to 200A. Cortical tissue: Close to 10D. Axillary buds: Close to N155C. Root description: Thick, fleshy contractile roots with few lateral branches; color, close to 155C. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Short to intermediate in height and upright to mounded plant habit; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants.*—About 18 cm to 21 cm.

*Plant height, from soil level to top of inflorescences, shadehouse-grown potted plants.*—About 28 cm.

*Plant diameter or spread, shadehouse-grown potted plants.*—About 30 cm to 33 cm.

*Number of shoots per plant, shadehouse-grown potted plants, tubers not de-eyed.*—About three to four develop per #1 tuber.

*Number of shoots per plant, shadehouse-grown potted plants, tubers de-eyed.*—About four to five develop per #1 tuber.

*Cataphylls, shadehouse-grown potted plants.*—Length: About 4.5 cm to 6 cm. Width: About 1 cm to 1.4 cm. Shape: Lanceolate to narrowly elliptic. Apex: Acute or emarginate. Base: Sheathing the stem. Color, inner surface: Close to N155B and 155C; colors and patterns on the outer surface are visible on the inner surface. Color, outer surface: Close to N155C to N155D and 199D, streaked and stippled with close to 200A tinged with close to 147D; with development, color becoming closer to 199A and 200B stained with close to 187A.

Leaf description:

*Arrangement and type.*—Alternate; simple; lance-type.

*Length, shadehouse-grown potted plants.*—About 11 cm to 15.5 cm.

*Width, shadehouse-grown potted plants.*—About 5.5 cm to 7.8 cm; when flattened, close to 7 cm to 9 cm.

*Shape.*—Ovate; folded upright along midvein.

*Apex.*—Acute to acuminate.

*Base.*—Sagittate to peltate.

*Margin.*—Entire; wavy with some broad undulations.

*Texture and luster, upper surface.*—Smooth, glabrous; with a dull sheen.

*Texture and luster, lower surface.*—Smooth, glabrous; glaucous with a dull sheen.

*Venation pattern.*—Pinnate.

*Color, shadehouse-grown potted plants.*—Developing and fully developed leaves, upper surface: Background color: Darker than 147A tinged with close to 137A. Leaf edge: Close to 187B. Basal notch: Close to 187B and 187C. Midvein: Close to 185B and 185C with random areas, close to N155C. Primary venation: Close to 185C, 185C tinged with close to 187C, 182B and 187C. Areas surrounding venation: Close to 184C, 184D, 185B, 185C and 155D. Interveinal areas: White, close to 155C; or green, close to 137B, 137C, 147B and 145D or red and greyed purple, close to 185B, 185C, 53B and 53C. Spots: Darker than 53A. Developing and fully developed leaves, lower surface: Background color: Close to 147B. Leaf edge: Close to 187B. Basal notch: Close to N186C. Midvein: Close to N155C and 194C. Primary venation: Close to 147D and 200D. Areas surrounding venation: Close to N155C and 155D. Interveinal areas: White, close to N155C and 155D; or green, close to 147C or greyed purple, close to 185B and 185C. Spots: Close to 59A.

*Petioles.*—Aspect: Initially upright and straight and outwardly leaning with development; flexible. Length, shadehouse-grown potted plants: About 13 cm to 17 cm. Diameter, distally, shadehouse-grown potted plants: About 3 mm to 3.5 mm. Diameter, proximally, shadehouse-grown potted plants: About 5 mm to 8 mm. Texture: Smooth, glabrous. Color, shadehouse-grown potted plants: When developing and fully developed: Close to 182D and N170D stippled, streaked and slightly tessellated with close to 200B tinged with close to 147A to 147B; distally, close to N170D tinged with close to 182D. Wing length, shadehouse-grown potted plants: About 3 cm to 4.7 cm. Wing diameter, shadehouse-grown potted plants: About 5 mm to 7.5 mm. Texture and luster, inner and outer surfaces: Smooth, glabrous; dull to slightly glossy. Wing color, shadehouse-grown potted plants: Inner surface: Close to 155C; colors and patterns on the outer surface are visible on the inner surface. Outer surface: Close to 182D and N170D stippled, streaked and tessellated with close to 200A tinged with close to 147A.

Inflorescence description: Inflorescences observed on six to seven week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about six to seven weeks after growth commences; inflorescences last about three days before fading; inflorescences persistent.

*Spathe*.—Length, overall: About 13 cm. Length, distal open portion: About 9.4 cm. Length, proximal closed portion: About 3.6 cm. Width, distal open portion: About 3.4 cm. Depth, distal open portion: About 1.9 cm. Width, at constriction: About 1.5 cm. Width, proximal closed portion: About 2.4 cm. Shape, open portion: Narrowly elliptic to ovate. Apex: Acuminate. Base: Acute. Margin: Entire; smooth. Texture and luster, front surface: Smooth, glabrous; dull sheen. Texture and luster, rear surface: Smooth, glabrous; distally, dull and proximally, glaucous. Color, front surface: Distal open portion: Close to 155B and 155C; with development, color becoming closer to 199A and 199B. Proximal closed portion: Close to 184D tinged with close to 145C; towards the base, faintly flushed with close to N186C; color does not change with development. Color, rear surface: Distal open portion: Close to 150D and 145D; color does not change with development. Proximal closed portion: Close to 147B, 147C and 146B; color does not change with development.

*Spadix*.—Length, overall: About 8 cm. Length, male flower zone: About 5 cm. Length, sterile zone: About 1.3 cm. Length, female flower zone: About 1.7 cm. Diameter, male flower zone: About 1 cm. Diameter, sterile flower zone: About 7 mm. Diameter, female flower zone: About 1.1 cm. Shape: Columnar, spindle-shaped. Apex: Rounded. Base: Obtuse. Aspect: Upright. Color, mature, male zone: Close to 155C to 155D. Color, mature, sterile zone: Close to 155D. Color, mature, female zone: Close to 158D and 158A. Male flowers: Quantity per spadix: About 145. Shape: Irregular in shape. Height: About 2.5 mm. Diameter: About 2 mm to 3 mm. Pollen amount: None observed. Female flowers: Quantity per spadix: About 150. Shape: Obovate. Height: About 2.5 mm. Diameter: About 2.5 mm. Stigma color: Close to 158D. Ovary color: Close to 158A.

*Scape*.—Length: About 15 cm. Diameter: About 7 mm. Strength: Sturdy; flexible. Aspect: Mostly erect. Texture and luster: Smooth, glabrous; slightly glossy. Color: Close to 148A and 147A, proximally streaked and stippled with close to 200B and 200C and tinged with close to N199A; distally, close to 147B and 147C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Heart and Soul' as illustrated and described.

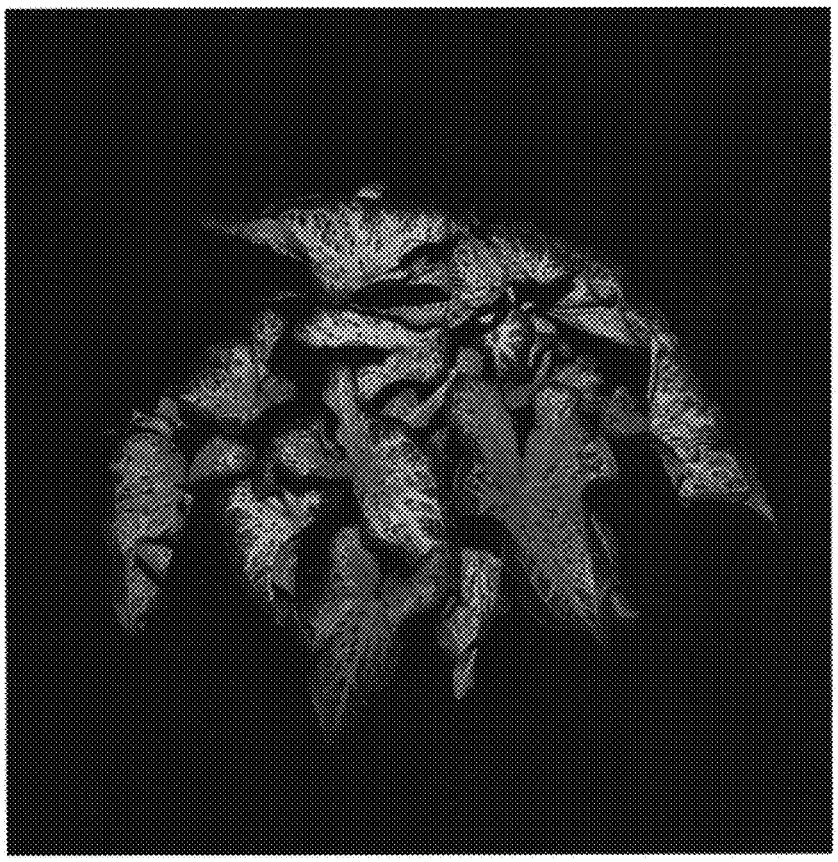

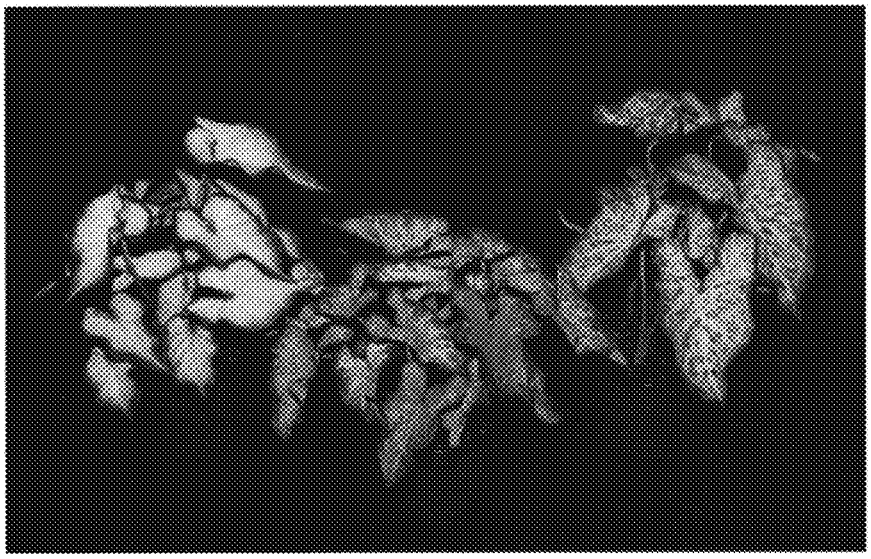
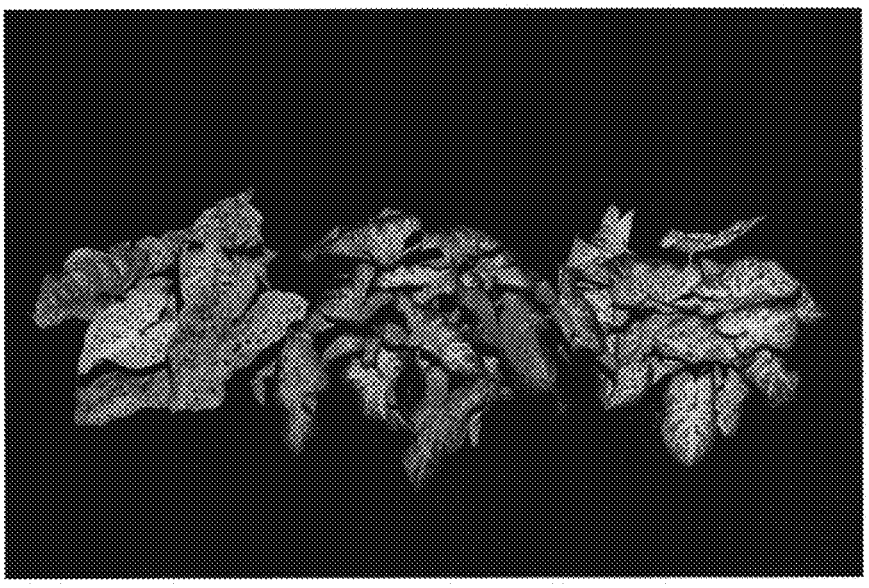

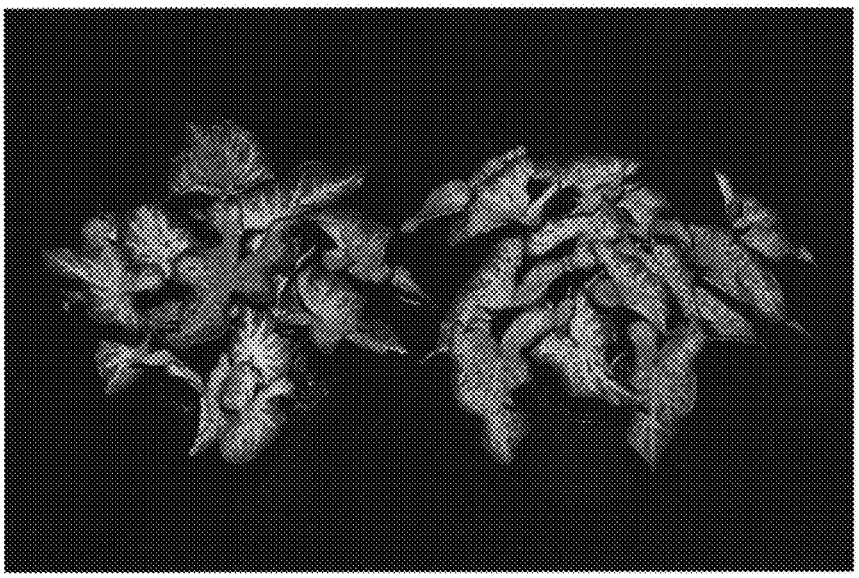
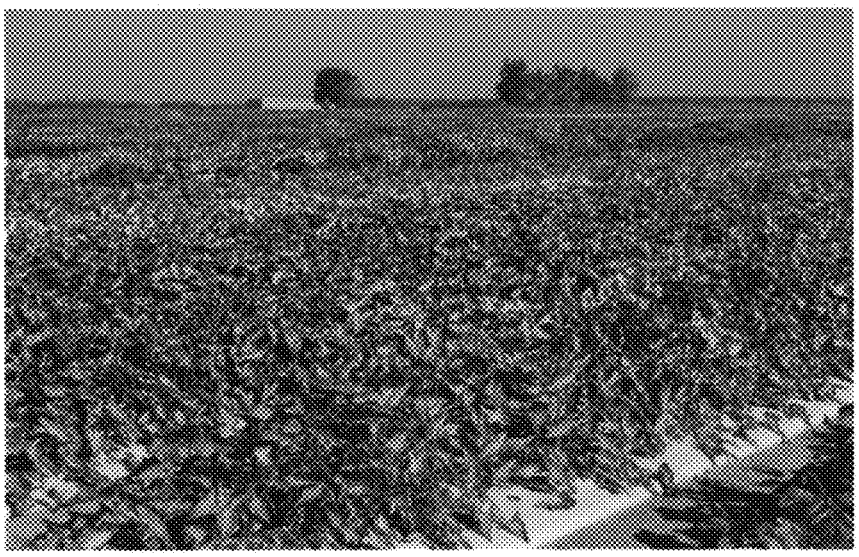

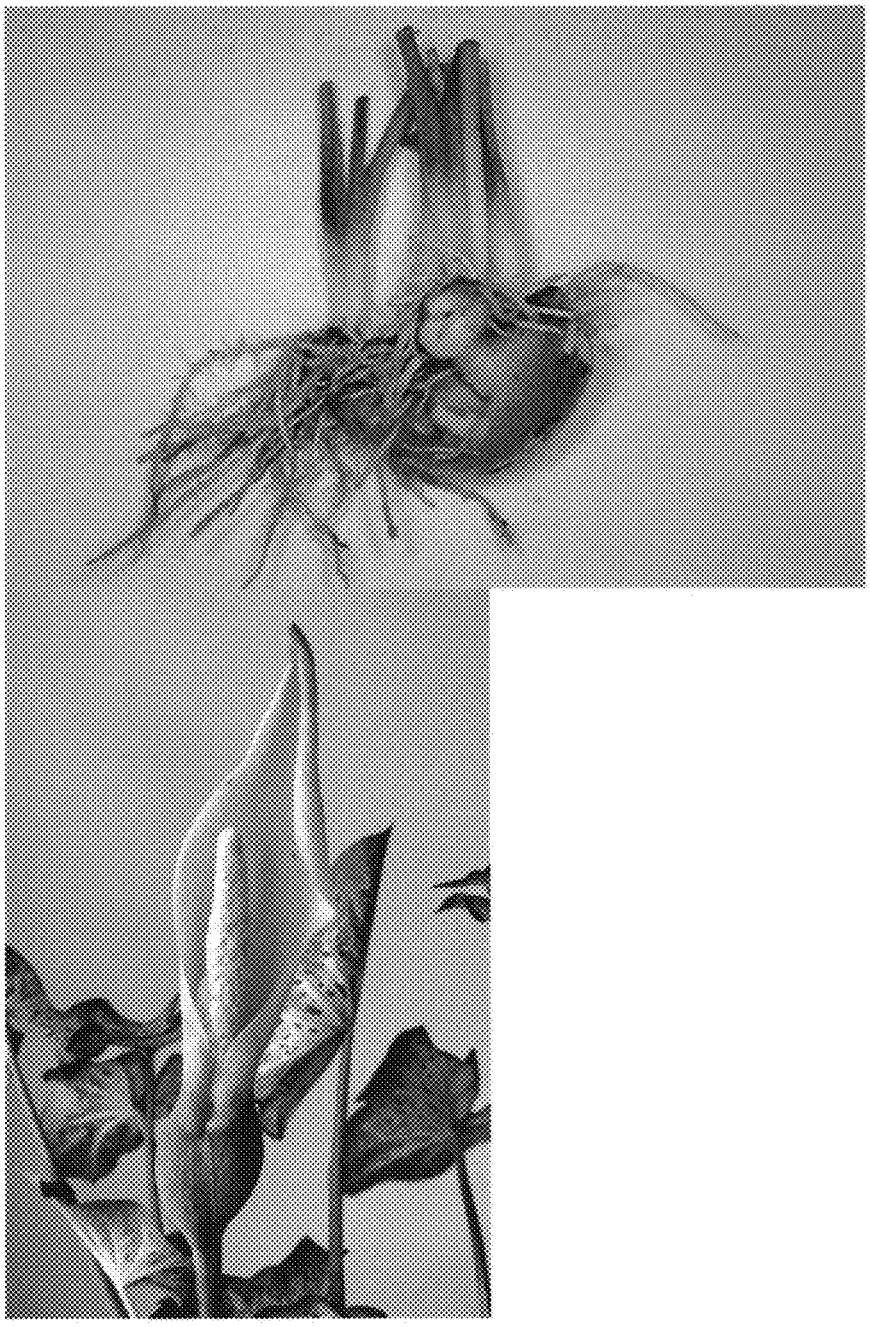

* * * * *